United States Patent [19]

Huang

[11] Patent Number: 5,020,994
[45] Date of Patent: Jun. 4, 1991

[54] DENTAL PROPHYLAXIS ANGLE

[76] Inventor: Jerry T. Huang, P.O. Box 3200, La Puenta, Calif. 91744

[21] Appl. No.: 477,238

[22] Filed: Feb. 9, 1990

[51] Int. Cl.$^5$ ............................................... A61C 1/08
[52] U.S. Cl. .................................. 433/126; 433/125; 433/128
[58] Field of Search ............... 433/124, 125, 126, 115, 433/80, 180, 127, 133

[56] References Cited

U.S. PATENT DOCUMENTS

| | | | |
|---|---|---|---|
| 3,727,313 | 4/1973 | Graham | 433/125 |
| 4,182,041 | 1/1980 | Girard | 433/125 |
| 4,348,180 | 9/1982 | Schuss | 433/126 |

*Primary Examiner*—Cary E. Stone
*Attorney, Agent, or Firm*—Timothy T. Tyson

[57] ABSTRACT

A dental prophylaxis angle formed of molded plastic parts is provided, which includes two accurately supported rotors extending at right angles to each other in an easily manufactured construction. The prophylaxis angle includes an elbow-shaped forward housing member (54, FIG. 2) which surrounds the output rotor (18) and the forward portion of the input rotor (14), and a rearward housing member (60) which snaps into arrangement with the rear of the forward housing member. The rearward housing member has a rotor-engaging shoulder (72) that can abut the shoulder (44) at the rear end of the input rotor forward portion.

4 Claims, 2 Drawing Sheets

DENTAL PROPHYLAXIS ANGLE

BACKGROUND OF THE INVENTION

One type of dental prophylaxis angle includes an elbow-shaped tubular housing with a forward tubular arm that supports an output rotor, and with a perpendicular tubular leg that supports an input rotor. The rotors have gears that mesh at the intersection of the tubular arm and leg. U.S. Pat. No. 3,163,934 by Wiseman shows an early version of this type of prophylaxis angle, which required the manufacture and installation of separate bearing parts to maintain the axial positions of the two rotors.

U.S. Pat. No. 3,727,313 by Graham describes an advanced dental prophylaxis angle construction, wherein the gear at the forward end of the input rotor served to fix the axial position of the output rotor, so no separate bearing was required to hold in the output rotor. That design used a hinged bearing that was pivoted out of the way to allow installation of the input rotor, with the bearing then pivoted through a slot in the housing to lie behind a rearward shoulder of the input rotor to prevent axial movement of the input rotor. However, the bearing extended only 90° about the axis of the input rotor, and therefore did not provide good support for the input rotor.

Another design for a molded dental prophylaxis angle used an elbow-shaped housing formed in two parts that each extended by 180° about the axes of the rotors. The rotors were installed in a first of the housing parts, and a second housing part then was placed over the first parts and the housing parts were heat welded together. One disadvantage of this design was the relatively high cost of manufacturing. A dental prophylaxis angle which had plastic molded parts that could be readily assembled, which provided a shoulder extending 360° about the rear end of the shoulder on the input rotor, and which formed accurate circular, or radial bearing portions for accurately supporting the rotors in rotation, would be of considerable value.

SUMMARY OF THE INVENTION

In accordance with one embodiment of the present invention, a relatively simple dental prophylaxis angle is provided which includes molded plastic housing members that accurately support input and output rotors of the prophylaxis angle. The prophylaxis angle includes molded plastic forward and rearward housing members and input and output rotors. The forward member forms a tubular elbow with a tubular arm holding the output rotor and with a largely perpendicular tubular leg supporting the forward portion of the input rotor. The rearward housing member fastens to the rear of the forward housing member. The rearward housing member receives the narrow shank at the rear of the input rotor, and has a shoulder that abuts the rearwardly-facing shoulder of the enlarged forward portion of the rotor.

The forward housing member can have rearwardly-projecting latch fingers at its rear end which are spread apart to receive the enlarged forward end of the input rotor. Then the fingers are projected through receptacle holes in the shoulder of the rearward housing member, until enlarged rearward ends of the latch finger snap into apertures in the rearward housing member, and a ring-shaped portion of the rearward housing member nests in recesses of the fingers.

The novel features of the invention are set forth with particularity in the appended claims. The invention will be best understood from the following description when read in conjunction with the accompanying drawings.

DESCRIPTION OF THE PREFERRED EMBODIMENT

Figure 1:
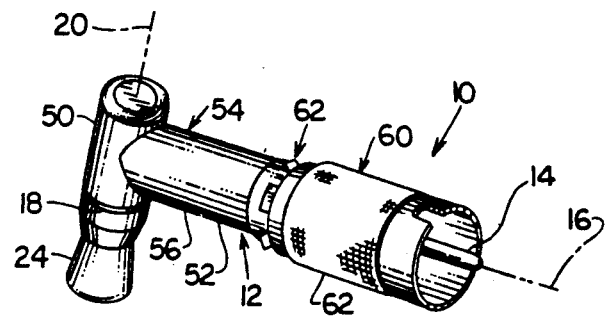
FIG. 1 is a perspective view of an assembled dental prophylaxis angle constructed in accordance with the present invention.

FIG. 1 illustrates a dental prophylaxis angle 10 of the present invention, which includes a tubular housing 12, an input rotor 14 mounted about an input axis 16 in the housing, and an output rotor 18 mounted about a perpendicular output axis 20. The output rotor carries a dental tool 24 such as a conventional elastic rubber cup that is used in polishing teeth.

Figure 2:
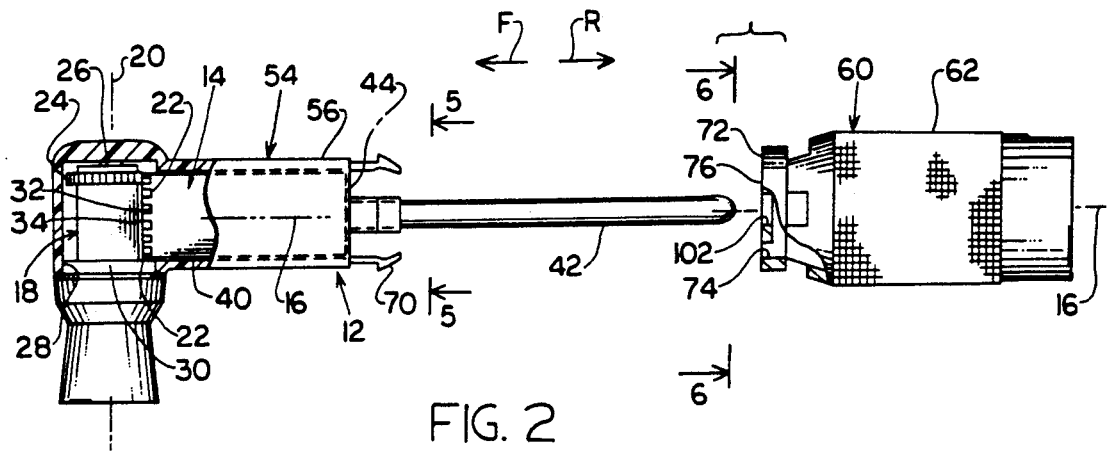
FIG. 2 is an exploded side view, partially in section, of the prophylaxis angle of FIG. 1.
Figure 2A:
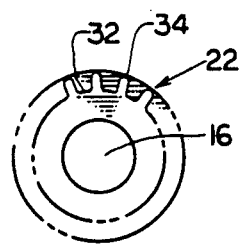
FIG. 2A is an end view of the input rotor of FIG. 2.

As shown in FIG. 2, the input rotor 14 has an input gear 22 that is meshed with an output gear 24 of the output rotor 18. The output rotor is maintained in rotation about the axis 20 by a bearing rod 26 that fits into a hole at the upper end of the output rotor. The output rotor is also rotatably supported by a bearing portion 28 of the housing, which closely surrounds a bearing surface 30 formed on a lower portion of the output rotor. The output rotor is prevented from falling down by the fact that the teeth of the output gear 24 rest on ledges 32 of the input gear which lie between teeth 34 of the input gear, as shown in FIG. 2A. This construction is known in the prior art. In order for the input gear 22 to remain engaged with the output gear, so as to drive the output rotor and support it from falling out, it is necessary that the input gear 22 not move more than a small amount along its axis of rotation 16.

The input rotor 14 (FIG. 2) has an enlarged forward rotor portion 40 and a reduced diameter rearward rotor portion or shank 42. The forward rotor portion 40 has a rearwardly-facing rotor shoulder 44. The input rotor is prevented from axial movement in a rearward direction R which is opposite to the forward direction F by forming the housing with a surface that abuts the rotor shoulder 44, as discussed below.

As can be seen in FIG. 2A, a region 45 of the input rotor forward portion that lies immediately rearward of the input gear, has the same outside diameter as the input gear. As shown in FIG. 2, the forward portion of the tubular leg closely surrounds the input rotor region 45 to serve as a radial bearing at a location immediately rearward of where the gears 22, 24 mesh.

As shown in FIG. 1, the tubular housing of the prophylaxis angle is elbow-shaped, with a forward tubular arm 50 extending along the output axis 20, and with a perpendicular tubular leg 52. Applicant constructs the housing so it is formed of two separately molded housing members, including a forward housing member 54 in the form of an elbow with the arm 50 and a forward portion 56 of the tubular leg 52, and with a separately molded rearward member 60 forming a rearward portion 62 of the tubular leg. The forward and rearward housing members 54, 60 form fastener portions 62 that hold the two housing members in tandem, in a securely attached and stable condition.

As shown in FIG. 2, the forward tubular portion housing member 54 includes four rearwardly-projecting latch fingers 70. The rearward housing member 60, or rearward tubular part 62 of the leg has a forward wall 72 with four receptacle holes 74 for receiving the four latch fingers 70. When the rearward housing member 60 is pushed forwardly, the latch fingers 70 enter the receptacle holes 74 and lock the forward and rearward housing members 54, 60 together.

Figure 3:
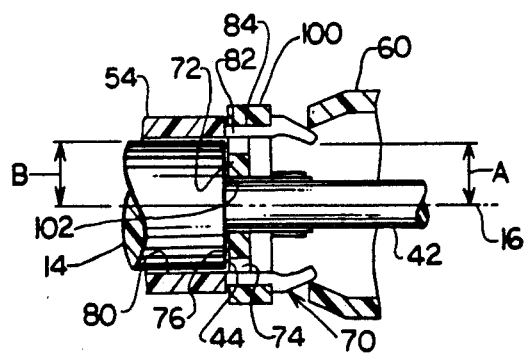
FIG. 3 is a sectional enlarged view of a portion of the prophylaxis angle of FIG. 2, shown in an assembled configuration.
Figure 6:
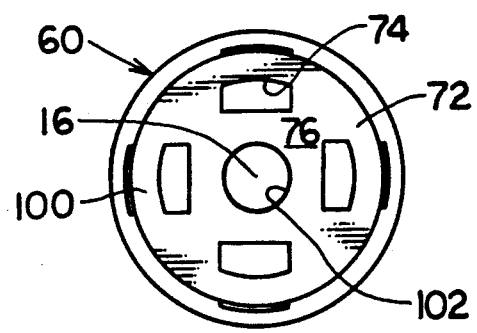
FIG. 6 is a view taken on the line 6—6 of FIG. 2.

FIG. 3 shows the housing members 54, 60 in an assembled condition wherein the latch fingers 70 lock the members together. In this configuration, a forwardly-facing rotor-engaging surface or shoulder 76 lies adjacent to the rearwardly-facing rotor shoulder 44. The rotor-engaging shoulder 76 then limits rearward movement of the input rotor 14 to prevent rearward axial movement of it that would cause the input gear to move out of meshing engagement with the output gear. As shown in FIG. 6, the rotor-engaging shoulder 76 can engage the rear of the rotor along an angle of 360° about the input axis 16. This enables effective backup of the rotor without pushing the rotor towards one particular side of the bearing hole 80 (FIG. 3) in the forward housing member which holds the forward rotor portion and serves to keep it centered on the input axis 16.

Figure 4:
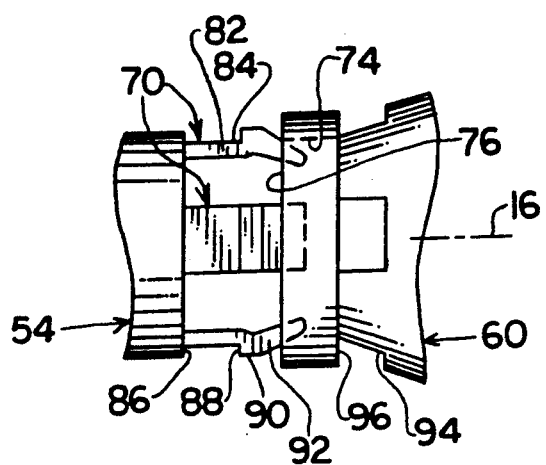
FIG. 4 is a side elevation view of the prophylaxis angle portion of FIG. 3, shown at the beginning of assembly of the housing members.
Figure 5:
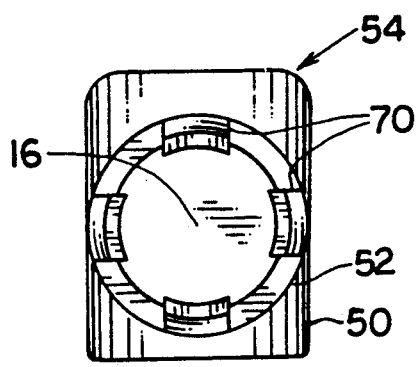
FIG. 5 is a view taken on the line 5—5 of FIG. 2.

As shown in FIG. 4, each latch finger 70 has a forward finger portion 82 with a recess 84 having opposite ends 86, 88 forming a pair of latch shoulders or abutments. Each latch finger also has a radially outward projection 90 and has an inwardly tapered rearward free end 92. When the forward and rearward housing members 54, 60 are first brought together while aligned with the axis 16, the walls of the receptacle holes 74 deflect the latch fingers radially inwardly towards the axis 16 until the finger projections 90 spring into apertures 94 in the rear housing member 60. At that time, the latch finger abutments 88 engage a rear member abutment 96 to prevent separation of the housing members (unless the latch fingers are first depressed).

With the forward and rearward housing members assembled as shown in FIG. 3, an interrupted ring-like forward part or end 100 of the rear member 60 lies in the finger recesses 84. It is noted that the forward finger portions 82 cannot deflect much. As a result, the ring 100 (it appears as a ring in the sectional side view of FIG. 3, but as an interrupted ring in FIG. 6) holds the rear housing member 60 to the front one, so the rear housing member remains coaxial with the front housing member and the axis 16.

The dental prophylaxis angle has four separately molded parts, these being the two rotors 14, 18 and the two housing members 54, 60. It is noted that the rubber cup 24 may be considered to be a separate tool. To assemble the parts, a person first inserts the input rotor 14 into the forward housing member 54. The minimum radius A of the latch fingers in their undeflected state is less than the radius B of the rotor at its input gear. Accordingly, the latch fingers 70 must be spread apart slightly in order to insert the forward rotor portion. A next step is to insert the output rotor 18, with the forward arm 50 oriented so it opens upwardly to keep the output rotor temporarily in place. A next step is to move the rearward housing member 60 forwardly along the input axis 16 so the rotor shank 42 projects through a central hole 102 in the forward wall 72 of the rearward housing member. The rearward housing member is moved forward until the housing members lie at the position shown in FIG. 4. The rear housing member 60 is pushed forwardly to allow the latch fingers 70 to pass through the receptacle holes 74 and snap into the apertures 94. The rotor-engaging shoulder 76 on the rear housing member then lies adjacent to the rotor shoulder 44 (FIG. 3), to hold the input rotor securely in position. Thus, the prophylaxis angle is formed from only four plastic parts that can be completely rigid except for the latch fingers. The rotor is held in axial position by a shoulder that extends completely around the input rotor axis to assure stable rotation of the input rotor.

The dental prophylaxis angle can be constructed at relatively low cost, and therefore can be made entirely disposable. The invention provides a dental prophylaxis angle with a minimal number of plastic molded parts that can be easily assembled and which holds the input rotor so it can stably rotate. The prophylaxis angle includes an elbow-shaped tubular housing with a forward tubular arm and a perpendicular tubular leg. The leg includes forward and rearward portions formed on separate forward and rearward housing members. The rear housing member has a forwardly-facing rotor-engaging shoulder that abuts a shoulder on the input rotor, and has a central hole through which the input rotor shaft projects. The front and rear housing members can be held together by latch fingers on one of them such as the forward member, which can project through reception holes in the rotor-engaging shoulder and which can spring into apertures in the rear housing member. The rear housing member has a ring-like forward end which can lie in recesses of the latch fingers to hold the rear housing part in a stable position relative to the front housing part.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. In a dental prophylaxis angle which includes an elbow-shaped tubular housing with a forward tubular arm and a tubular leg extending in a predetermined rearward direction from said arm, an output rotor rotatably mounted in said forward arm and having an output gear, an input rotor rotatably mounted in said leg about an axis extending in forward and rearward directions, said input rotor also having an input gear engaged with said output gear to drive it, the improvement wherein:

said housing includes separate forward and rearward tubular housing members forming forward and rearward portions of said tubular leg, and fastener portions that join said housing members to lie in tandem;

said input rotor has forward and rearward rotor portions lying respectively in said forward and rearward housing members, said forward rotor portion having a rearwardly-facing rotor shoulder, and said rearward rotor portion forming a shaft of smaller diameter than said rotor shoulder;

said forward rotor portion has an extreme front end with cutouts forming teeth which comprise said input gear, and said forward rotor portion includes a region immediately rearward of the location where the teeth of said gear mesh, which has an outside diameter at least as great as the outside of said input gear, and said forward portion of said tubular leg closely surrounds said forward rotor region to serve as a radial bearing, whereby to rotatably support said input rotor very close to said input gear thereon.

2. A dental prophylaxis angle comprising:

a housing which includes molded plastic forward and rearward housing members, said forward member being in the form of a tubular elbow with an arm and a leg extending in a predetermined rearward direction from said arm, said arm and leg extending at primarily a right angle to each other;

an output rotor lying in said arm of said forward housing member;

an input rotor having a large diameter rotor forward portion lying in said leg of said forward housing member and coupled to said output rotor to rotate it, and having a smaller diameter shank extending rearwardly from said rotor forward portion, said input rotor being rotatable about an axis extending in forward and rearward directions and forming a rearwardly-facing shoulder facing rearwardly along said axis;

said leg of said forward housing member having a rear portion forming a plurality of rearwardly-extending latch fingers, each finger including a recess with forward and rearward recess ends, and each finger having a rearward end;

said rearward housing member having a forward tubular portion with a forward end wall having a surface extending perpendicular to said axis and forming a forwardly-facing shoulder for abutting said rotor shoulder, said end wall having a central hole through which said shank extends and a plurality of receptacle holes spaced radially outward with respect to said axis from said central hole for receiving said latch fingers;

said forward tubular portion of said rearward housing member having a plurality of apertures spaced rearwardly from said end wall at locations to receive said rearward ends of said fingers to lock said housing members together, and said forward tubular portion having a ring-like part that rests in said recesses of said fingers.

3. In a dental prophylaxis angle which includes an elbow-shaped tubular housing with a forward tubular arm and a tubular leg extending in a predetermined rearward direction from said arm, an output gear, an input rotor rotatably mounted in said leg about an axis extending in forward and rearward directions, said input rotor also having an input gear engaged with said output gear to drive it, the improvement wherein:

said housing includes separate forward and rearward tubular housing members forming forward and rearward portions of said tubular leg, and fastener portions that join said housing members to lie in tandem;

said input rotor has forward and rearward rotor portions lying respectively in said forward and rearward housing members, said forward rotor portion having a rearwardly-facing rotor shoulder, and said rearward rotor portion being of smaller diameter than said rotor shoulder;

said rearward housing member has a front wall that forms a forwardly-facing rotor-engaging shoulder that abuts said input rotor shoulder, said front wall having a central hole through which said rearward rotor portion projects;

said forward housing member includes a plurality of rearwardly-projecting latch fingers;

said front wall of said rearward housing member has a plurality of receptacle holes that receive said latch fingers to latch said forward and rearward housing members together, said latch fingers and receptacle holes forming said fastener portions of said housing;

said latch fingers have portions closest to said axis which lie closer to said axis than the radius of said input gear, so said latch fingers must deflect radially outwardly away from said axis to install said forward input rotor portion in said forward housing member;

said receptacle holes are close enough to said axis that said latch fingers are deflected radially inwardly toward said axis as they enter said receptacle holes.

4. In a dental prophylaxis angle which includes an elbow-shaped tubular housing with a forward tubular arm and a tubular leg extending in a predetermined rearward direction from said arm, an output rotor rotatably mounted in said forward arm and having an output gear, an input rotor rotatably mounted in said leg about an axis extending in forward and rearward directions, said input rotor also having an input gear engaged with said output gear to drive it, the improvement wherein:

said housing includes separate forward and rearward tubular housing members forming forward and rearward portions of said tubular leg, and fastener portions that join said housing members to lie in tandem;

said input rotor has forward and rearward rotor portions lying respectively in said forward and rearward housing members, said forward rotor portion having a rearwardly-facing rotor shoulder, and said rearward rotor portion being of smaller diameter than said rotor shoulder;

said rearward housing member has a front wall that forms a forwardly-facing rotor-engaging shoulder that abuts said input rotor shoulder, said front wall having a central hole through which said rearward rotor portion projects;

said forward housing member includes a plurality of rearwardly-projecting latch fingers;

said front wall of said rearward housing member has a plurality of receptacle holes that receive said latch fingers to latch said forward and rearward housing members together, said latch fingers and receptacle holes forming said fastener portions of said housing.

* * * * *